(12) United States Patent
Makowski

(10) Patent No.: US 11,933,925 B2
(45) Date of Patent: Mar. 19, 2024

(54) PARTICLE ENERGY MEASURING DEVICE AND METHOD FOR DETERMINING A BEAM ENERGY OF A PARTICLE BEAM

(71) Applicant: BUNDESREPUBLIK DEUTSCHLAND, VERTRETEN DURCH DAS BUNDESMINISTERIUM FUR WIRTSCHAFT UND ENERGIE, DIESES VERTRETEN DURCH DEN PRASIDENTEN DER PHYSIKALISCH-TECHNISCHEN BUNDESANSTALT, Braunschweig (DE)

(72) Inventor: Christoph Makowski, Braunschweig (DE)

(73) Assignee: BUNDESREPUBLIK DEUTSCHLAND, VERTRETEN DURCH DAS BUNDESMINISTERIUM FUR WIRTSCHAFT UND ENERGIE, DIESES VERTRETEN DURCH DEN PRASIDENTEN DER PHYSIKALISCH-TECHNISCHEN BUNDESANSTALT, Braunschweig (DE)

( * ) Notice: Subject to any disclaimer, the term of this patent is extended or adjusted under 35 U.S.C. 154(b) by 301 days.

(21) Appl. No.: 17/617,756

(22) PCT Filed: Jun. 11, 2019

(86) PCT No.: PCT/EP2019/065254
§ 371 (c)(1),
(2) Date: Dec. 9, 2021

(87) PCT Pub. No.: WO2020/249194
PCT Pub. Date: Dec. 17, 2020

(65) Prior Publication Data
US 2022/0236429 A1 Jul. 28, 2022

(51) Int. Cl.
*G01T 1/24* (2006.01)
*G01T 1/29* (2006.01)
*A61N 5/10* (2006.01)

(52) U.S. Cl.
CPC .............. *G01T 1/242* (2013.01); *G01T 1/29* (2013.01); *A61N 5/1075* (2013.01)

(58) Field of Classification Search
CPC ......... A61N 5/1075; G01T 1/242; G01T 1/29; G01T 1/00; G01T 3/00; G01T 5/00; G01T 7/00
See application file for complete search history.

(56) References Cited

U.S. PATENT DOCUMENTS

| 5,308,988 | A | 5/1994 | Siedband |
| 2008/0283764 | A1 | 11/2008 | Kerwin |
| 2018/0164445 | A1 | 6/2018 | Sacchi |

*Primary Examiner* — Lee E Rodak
*Assistant Examiner* — Brent J Andrews
(74) *Attorney, Agent, or Firm* — WCF IP

(57) ABSTRACT

The invention relates to a particle energy measuring device (14) for determining the energy of a particle beam (26) with (a) at least twenty capacitors (30.$n$) that (i) each comprise a first capacitor plate (32.$n$) and (ii) a second capacitor plate (34.$n$), and (iii) are arranged one behind the other with respect to a beam incidence direction (S), (b) a multiplexer (46) that has (i) a multiplexer outlet (48) and (ii) a plurality of multiplexer inputs (50.$n$), each multiplexer input (50.n) being designed to connect to precisely one capacitor (30.$n$) and (iii) that is configured to connect one of the capacitor plates (32.$n$, 34.$n$) of the respective capacitor to the multiplexer outlet (48), (c) a total charge measuring device (52) that (i) comprises a total charge measuring device input (54), which is connected to the second capacitor plates (34.$n$) in order to detect a total charge ($Q_\Sigma$) of the charges on all the capacitors (30.$n$), and (d) a total charge measuring device outlet (56), and (d) an analysis circuit (58) that (i) is connected to the total charge measuring device (52) and the multiplexer (46), and is designed to automatically (i) effect (Continued)

Figure 1:
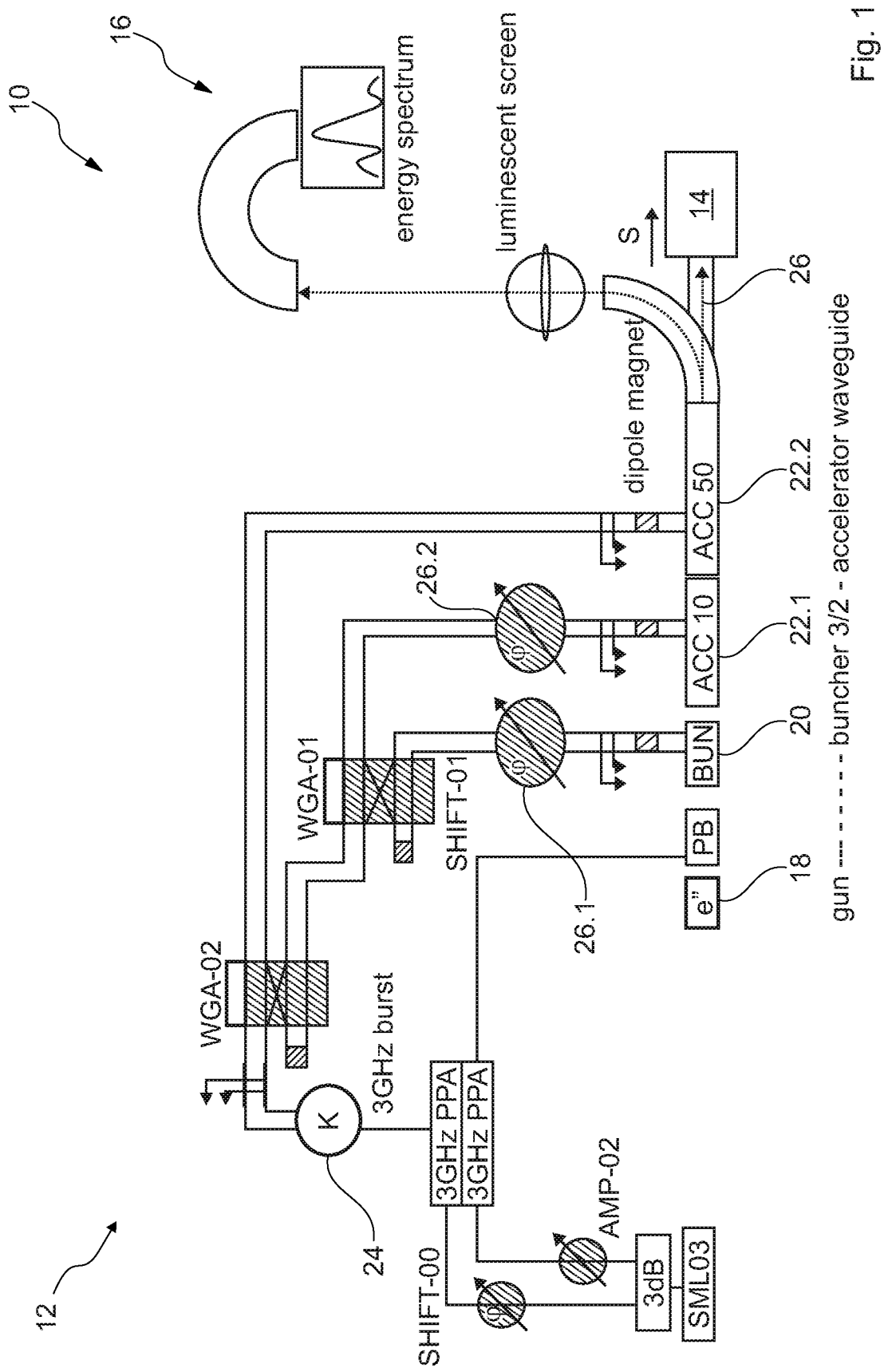

a switch from one multiplexer input (50.$n$) to another multiplexer input (50.$n$), so that the capacitors are individually discharged in succession and (ii) detect the charge ($Q_n$) flowing from each capacitor (30.$n$) during the discharging process, thereby obtaining charging data from which the particle energy (E) can be calculated.

28 Claims, 8 Drawing Sheets

PARTICLE ENERGY MEASURING DEVICE AND METHOD FOR DETERMINING A BEAM ENERGY OF A PARTICLE BEAM

Particle accelerators are used in particular in research and medicine to generate a particle beam from particles of a given energy. In medical applications, the particle beam is used to destroy tissue in a targeted manner. To protect nearby tissue, the particle energy must be known to a high degree of accuracy. It is also necessary to know the number of particles—or as an equivalent the overall charge of the particle beam—to be able to calculate the dose applied to the tissue.

Accelerators are composed of a number of components. Even small changes to the position of the components relative to each other have a considerable impact on the particle energy. It is therefore necessary to adjust accelerators at least upon commissioning, but generally also at regular intervals. Adjustment not only refers to the purely mechanical alignment, but also to subsequent adjustments, for example to mostly existing focus and deflection electromagnets, phase shifters, RF power controllers and/or the particle source. These all directly affect the energy and power of the beam and must be operated frequently during normal operation.

Due to the number of components, whose relative positions to each other are relevant, and the fact that the impact of a change in the position of a component relative to the others is usually unknown, a large number of test measurements must be conducted to achieve an effective alignment of the individual components of the particle accelerator relative to each other.

Since a large number of test measurements must be conducted, the duration of each individual test measurement is highly relevant for the overall duration of the adjustment. Particle energy measuring devices should therefore have both a low measurement uncertainty and allow for a short measurement time.

The invention aims to improve the measurement of particle energy and the particle beam.

The invention solves the problem by way of a particle energy measuring device for determining the energy of a particle beam with (a) at least twenty capacitors that (i) each comprise a first capacitor plate and (ii) a second capacitor plate, and (iii) are arranged one behind the other with respect to a beam incidence direction, (b) a multiplexer that has (i) a multiplexer outlet and (ii) a plurality of multiplexer inputs, each multiplexer input being designed to connect to precisely one capacitor and (iii) that is configured to connect one of the capacitor plates of the respective capacitor to the multiplexer outlet, (c) a total charge measuring device that (i) comprises a total charge measuring device input, which is connected to the second capacitor plates in order to detect a total charge of the charges on all the capacitors, and (ii) a total charge measuring device outlet, and (d) an analysis circuit that is connected to the total charge measuring device and the multiplexer, and is designed to automatically (i) effect a switch from one multiplexer input to another multiplexer input, so that the capacitors are individually discharged in succession and (ii) detect the charge flowing from each capacitor during the discharging process, thereby obtaining charging data from which the particle energy can be calculated.

According to a second aspect, the invention solves the problem by way of a method for determining a beam energy of a particle beam, the successive measurement of the charges of the capacitors being achieved by switching the total charge measuring device to detect a total charge of all charges on the capacitors, successively discharging all capacitors and measuring the decrease in the total charge for the discharge of one capacitor at a time for the discharge of all capacitors. The measurement of the decrease in the total charge for the discharge of one capacitor at a time for the discharge of all capacitors is understood particularly to mean that the decrease in the total charge for the discharge of one capacitor is measured and this is conducted for all capacitors.

The invention also solves the problem by way of a method for determining a beam energy of a particle beam featuring the steps: (a) allowing the particle beam to fall on a particle energy measuring device that comprises (i) at least twenty capacitors ($30.n$), which each comprise a first capacitor plate and a second capacitor plate, and are arranged one behind the other with respect to a beam incidence direction (S), (ii) a multiplexer that has a multiplexer outlet and a plurality of multiplexer inputs, wherein each multiplexer input can be connected to precisely one capacitor and said multiplexer is configured to connect one of the capacitor plates of the respective capacitor to the multiplexer outlet, (iii) a plate charge measuring device that comprises a plate charge measuring device input, which is connected to the second capacitor plates, and a plate charge measuring device outlet, (b) successively measuring the capacitor charges by means of the plate charge measuring device by successively connecting the capacitors to the plate charge measuring device by means of the multiplexer, thereby obtaining charge data, and (c) calculating the particle energy and/or a beam charge from the charge data.

The advantage of the solution according to the invention is that a low degree of measurement uncertainty can be achieved. Specifically, it has been proven that a high degree of measurement accuracy can be achieved when a large number of capacitors is provided. For example, the particle energy measuring device preferably comprises 64 capacitors, especially preferably 100 capacitors. It is beneficial if there is a maximum of 1000 capacitors.

Another advantage is that very short measuring times can be achieved. In this way, it is possible to measure the particle energy with a measuring time of less than one minute, particularly less than ten seconds, particularly even less than one second. This allows, for example, for a significantly quicker adjustment of a particle accelerator.

It is also beneficial that the effort required for the calibration of a particle energy measuring device according to the invention is usually relatively small. This is because only a charge measuring device needs to be calibrated, which can be achieved with a high degree of accuracy. Theoretically, it would be possible to provide a number of charge measuring devices, which could lead to an even shorter measuring time. However, the disadvantage of this is that the calibration of the individual charge measuring devices in this case requires considerable effort.

A further advantage is that in most cases a good signal-to-noise ratio can be achieved. The greater the charge that accumulates on a single capacitor, the lower the noise level with which this charge can be measured. It is therefore practical to apply the particle beam to the detector until a sufficiently high number of charges has formed on the capacitors.

If no total charge measuring device is used, however, waiting too long could cause the charge accumulated on the capacitors to become so great that the resulting electrical field is above the breakdown threshold, resulting in a breakdown. The capacitor is then destroyed and the particle energy measuring device no longer delivers reliable data. If a total charge measuring device is used, the total charge can be used to determine the ideal time for reading the capacitors, i.e. determining their charge, which represents a preferred embodiment of the method according to the invention. This renders it possible to point the particle beam on the particle energy measuring device until there is a sufficiently high charge on the capacitors, so as to obtain a high signal-to-noise ratio.

The total charge measuring device is understood to be a charge integrator, in particular a cyclical charge integrator. The term should indicate that this charge integrator is used to measure the total charge across all capacitors. The total charge measuring device could also be referred to as a first integrator.

The plate charge measuring device is also understood to be a charge integrator, in particular a cyclical charge integrator. The term should indicate that this charge integrator is used to measure the charge on the plates of a single capacitor. The plate charge measuring device could also be referred to as a second integrator.

The feature that the particle energy measuring device is a particle energy measuring device for determining the energy of a particle beam is understood particularly to mean that the particle energy measuring device can be used to measure the energy and preferably also outputs the energy as a measurement result. It is beneficial if the particle energy measuring device can also output quantities that can be calculated from measured quantities such as charge and energy, for example beam output, absorbed dose and/or fluence.

It is beneficial if the capacitors have a solid dielectric. The solid dielectric is preferably an oxide layer applied to one or both capacitor plates. For example, if one capacitor plate is made of aluminium, the dielectric is preferably formed by an anodized layer. The anodized layer could then be metallized, for example with copper, which forms the second capacitor plate.

It is noted for all embodiments that the capacitor plates do not have to be separable from each other. It is also possible that the capacitor plates are connected, especially inseparably, to each other. In particular, at least one capacitor plate can be designed as a coating of another object, for example the other capacitor plate.

Alternatively, the solid dielectric may be formed by a plastic plate. The plastic plate preferably contains more than 95% by weight of molecules that do not contain atoms with a nuclear charge number greater than nine. It is especially beneficial if the plastic plates are made of halogen-free plastic. The smaller the nuclear charge number, the smaller the interaction with particle beams, so that processes occurring in the dielectric have only a small impact on measurement uncertainty. Preferably, the plastic plates are made of PET (polyethylene terephthalate).

It is especially beneficial if the first capacitor plate, the solid dielectric and the second capacitor plate are bonded together to form capacitors. It is then possible to stack the individual capacitors on top of each other, so that the particle energy measuring device can be produced relatively easily. It is then also possible to replace individual capacitors with little effort if they are defect.

According to a preferred embodiment, the particle energy measuring device comprises an analysis circuit that is designed to automatically conduct a method featuring the step of detecting the charge flowing from the respective capacitor by forming the difference between the charge on the total charge measuring device at the beginning and end of the discharging process of the respective capacitor, wherein this step is conducted for each position of the multiplexer and thus for all capacitors. In this way, charge data is obtained.

The charge data preferably encode the charge of each capacitor and contain an identifier, by means of which the respective capacitor can be identified. This identifier can also be encoded, for example, in that the charge data is output in a predetermined order and the order in which the capacitors are read is constant and known.

Advantageously, the multiplexer outlet is directly connected to earth. The first and second capacitor plates of the corresponding capacitor are thus connected to each other via the multiplexer and the total charge measuring device. In this way, only one total charge measuring device, i.e. an integrator, is necessary, which reduces the effort required for calibration.

The analysis circuit is preferably designed to control the multiplexer such that it successively discharges the capacitors when the analysis circuit receives a trigger signal. A trigger signal is understood to mean a signal that encodes the fact that a particle beam is emitted from the accelerator within a predetermined interval around the time of the trigger signal.

It is beneficial if the particle energy measuring device (a) has a plate charge measuring device that (i) comprises a plate charge measuring device input, which is connected to the multiplexer outlet, and (ii) a plate charge measuring device outlet, and which (iii) is designed to measure a charge that flows via the multiplexer outlet and the plate charge measuring device input. It is beneficial, but not necessary, if the reference ground of the total charge measuring device outlet is at the same electrical potential as that of the plate charge measuring device outlet.

It is favourable for the analysis circuit to be connected to the total charge measuring device and the multiplexer and to be designed to automatically detect the charge flowing from each capacitor by detecting the charge measured by the plate charge measuring device. In this way, charge data is obtained. By means of the plate charge measuring device, the charge on the capacitor plates can be measured with a particularly high degree of accuracy. It should be noted that in this case it possible, but not necessary, that the particle energy is calculated exclusively from the charge data collected by the plate charge measuring device. The total charge measuring device can then be used, for example, to identify the ideal time for a measurement. To this end, the analysis circuit is preferably designed to automatically read the charges of the capacitors in succession when the charge measured by the plate charge measuring device has exceeded a predetermined limit. As described above, this is achieved by successively connecting the capacitors to the plate charge measuring device by means of the multiplexer, so that the charge stored by the respective capacitor is detected by the plate charge measuring device and the capacitor discharged.

According to a preferred embodiment, the plate charge measuring device and total charge measuring device are used to determine the charges of the capacitors. The advantage of using both charge measuring devices is that it reduces measurement uncertainty. This is particularly true if more than one measurement per second is conducted and/or the pulse charging of a particle beam is small. The charges on the individual capacitors are considerably smaller than the total charge, but the measurement range of the plate charge measuring device is preferably set to be more sensitive by a factor of 10. The sum of the individual channel charges provides a second, independent value for the total beam charge, which leads to a redundancy of the charge measurement.

It is beneficial if the analysis circuit is designed to automatically discharge the capacitors if no trigger signal is received after a predetermined shut-down period has passed. This minimises the risk of one of the capacitors being charged too much.

The effective depth is understood to mean an indication of depth for which it holds that two plates of different densities and/or different thicknesses have exactly the same effect on the particles when the effective thicknesses of the two plates are the same. Given that the strength of the interaction between the particles and the material depends, in good approximation, on the density of the latter, the effective depth is preferably the product of the density and absolute depth. In particular, the effective depth is understood to mean the product of the absolute depth, i.e. a length, and the density of the material through which the beam extends. If, for example, the particle beam extends through aluminium, the effective depth is the product of the density of aluminium and the path covered by the beam in the aluminium.

Alternatively or additionally, the analysis circuit is preferably designed to automatically calculate the particle energy from the charge data via the steps (i) determining a width parameter of the charge function and (ii) determining the particle energy from the width parameter. The width parameter is understood to mean a number that indicates how wide the charge function is over a depth, particularly over the effective depth. If the particles exhibit a high particle energy, they can still ionize at greater effective depths. The width of the charge function is therefore a good measure of particle energy.

The determination of the width parameter is preferably achieved by numerically determining the integral under the normalized charge function. Normalizing causes the width parameter to become independent of the total charge, i.e. the sum of all charges on the capacitors. For example, normalizing is achieved by dividing by the maximum value of the charge function. It is also possible that the charge function is fitted with a model function (also referred to as data fitting) and, for the purpose of normalizing, the charge function is then divided by the maximum value of the determined balance function.

A specific capacity of the capacitors is preferably 30 to 100 Picofarad per square centimeter. Alternatively or additionally, the capacity is at least 1 Nanofarad, especially at least 7 Nanofarad. This allows for a favorable signal-to-noise ratio. The capacity is preferably smaller than 100 Nanofarad. This keeps the effort required to produce the capacitor within a reasonable scope.

Due to the specified capacity and/or specific capacity, it is possible to accumulate the charges in the capacitors. This facilitates the sequential reading of the channel charges with only one integrator. With low plate capacities, parallel measurements should preferably be taken, as even small charges build up high voltages. With parallel readings, the charge is permanently discharged from the capacitor. With such a design, however, each integrator would have to be like the other, especially with regard to the respective leakage current, otherwise the measured charge profiles would become noisy and an energy measurement would be afflicted with a high measurement uncertainty.

An insulation resistance between the first capacitor plate and the second capacitor plate is preferably at least one gigaohm. Preferably, this applies to at least 90% of the capacitors, particularly for all capacitors. The high resistance between the capacitor plates of a capacitor means that no significant amount of charge is lost during the measurement. It is not essential for the insulation resistance to be greater than 10 gigaohm.

To achieve low measurement uncertainty, it is beneficial if a capacity of the capacitors is greater, in particular by a factor of at least 5, than an intermediate capacitor capacity, between capacitor plates of adjacent capacitors.

It has been proven to be beneficial if at least a majority of the first capacitor plates are made predominantly of copper and/or aluminium. The first capacitor plate is preferably the beam-side capacitor plate of the corresponding capacitor.

The particle energy measuring device preferably has an irradiation side. This irradiation side is, for example, labeled on the particle energy measuring device or specified in an operating manual. It is favorable if an area-related density of the capacitor plate on the irradiated side (with respect to a beam incidence direction S) is greater than an area-related density of the capacitor plate of the capacitor facing away from the beam, preferably by at least a factor of 2, particularly preferably by at least a factor of 3.

It is favorable if it holds for at least two, especially for at least a majority of the capacitor plates, that an effective thickness of the capacitor plate facing away from the beam is smaller than an effective thickness of the beam-side capacitor plate. The effective thickness is the actual thickness of the capacitor plate multiplied by the density of the material from which the capacitor plate is made. The effective thickness of the beam-side capacitor plate is preferably at least twice as great as the effective thickness of the capacitor plate facing away from the beam.

It is beneficial if the beam-side capacitor plate has a lower density than the capacitor plate facing away from the beam.

For example, the effective thickness of the beam-side aluminum capacitor plate is between 0.3 and 3 grams per cubic centimeter and the effective thickness of the capacitor plate facing away from the beam is between 0.15 and 0.35 grams per cubic centimeter.

For example, the beam-side capacitor plate is made of graphite or aluminium. A density of the beam-side capacitor plate is preferably at most 3 grams per cubic centimeter. Preferably, the density of the capacitor plate facing away from the beam is also at most 3 grams per cubic centimeter.

Preferably, it holds for at least two capacitors, in particular at least 20, that an effective thickness of at least one capacitor plate of the capacitor facing away from the beam is greater than the effective thickness of at least one capacitor plate of the beam-side capacitor. This increases the resolution of the energy in particle energies.

It is especially favorable if it holds for at least two capacitors, in particular at least 20, that an effective thickness of the beam-side capacitor plate of the capacitor facing away from the beam is greater than the effective thickness of the beam-side capacitor plate of the beam-side capacitor.

A particle energy measuring device according to the invention preferably has a calibration certificate in which the measurement uncertainty for at least one particle energy is stated. In particular, the calibration certification preferably contains (a) the measurement uncertainty for at least one particle energy and/or (b) a width calibration factor, by means of which the particle energy can be calculated from the width parameter.

The analysis circuit is preferably designed to automatically effect a discharge of the capacitors, at least if the total charge exceeds a predetermined charge limit. This protects the capacitors from too great a voltage. The charge limit preferably corresponds to a voltage of 10±1 Volt on the total charge measuring device.

It is beneficial if the analysis circuit is also designed to automatically effect a discharge of the capacitors if (i) the supply voltage for the electronics is missing, (ii) the trigger signal is missing, (iii) a trigger frequency is too high, so that a pulse overlap can occur, and/or (iv) the integrator signal has a voltage of over 10V.

The invention also includes an accelerator system with a particle accelerator, in particular a linear accelerator, for generating a monoenergetic particle beam and a measurement device according to the invention, which is arranged to measure a particle energy of particles of the particle beam and/or a beam charge of the particle beam. The particle accelerator is preferably an electron, proton or ion accelerator. The analysis circuit is preferably configured to automatically conduct a method according to the invention. The particle beam is preferably composed of charged particles, particularly electrons, protons or ions. The particle beam can be continuous. The particle beam is preferably pulsed.

A method according to the invention is preferably conducted in such a way that a particle beam made up of particles with an average particle energy is generated and a particle energy measuring device is used whose capacitor plates together are so thick that a total collecting efficiency for the particles with an average particle energy is at least 95%. In other words, this means that a maximum of 5% of all particles cross the particle energy measuring device without being absorbed.

The average particle energy is preferably between 2 megaelectronvolts and 1500 megaelectronvolts.

The invention also includes a particle energy measuring device for determining a particle beam with (a) at least twenty capacitors that (i) each comprise a first capacitor plate and (ii) a second capacitor plate, and (iii) are arranged one behind the other with respect to a beam incidence direction, (b) a multiplexer that has (i) a multiplexer outlet and (ii) a plurality of multiplexer inputs, each multiplexer input being connected to precisely one capacitor and (iii) that is configured to connect a first capacitor plate of the respective capacitor to the multiplexer outlet, (c) a plate charge measuring device that (i) comprises a plate charge measuring device input, which is connected to the multiplexer outlet, and (ii) a plate charge measuring device outlet, and (iii) is designed to measure a charge flowing via the multiplexer outlet and the plate charge measuring device, (d) an analysis circuit that is connected to the plate charge measuring device and the multiplexer, and is designed to automatically (i) effect a switch from one multiplexer input to another multiplexer input, so that the capacitors are individually discharged in succession and (ii) detect the charge flowing from each capacitor during the discharging process, thereby obtaining charging data from which the particle energy can be calculated.

It is possible, but not necessary, that this particle energy measuring device features a total charge measuring device that comprises a total charge measuring device input, which is connected to the second capacitor plate and designed to detect a total charge of the capacitors, and a total charge measuring device outlet. The preferred embodiments of particle energy measuring devices described above also apply for this invention.

The invention also includes a particle energy measuring device with (a) at least twenty capacitors that (i) each comprise a first capacitor plate and (ii) a second capacitor plate, and (iii) are arranged one behind the other with respect to a beam incidence direction, (b) a multiplexer that has (i) a multiplexer outlet and (ii) a plurality of multiplexer inputs, each multiplexer input being connected to precisely one capacitor and (iii) that is configured to connect a first capacitor plate of the respective capacitor to the multiplexer outlet, (c) a plate charge measuring device that (i) comprises a plate charge measuring device input, which is connected to the multiplexer outlet, and (ii) a plate charge measuring device outlet, and (iii) is designed to measure a charge flowing via the multiplexer outlet and the plate charge measuring device outlet, and (d) a total charge measuring device that comprises (i) a total charge measuring device input, which is connected to the two capacitor plates for detecting a total charge of the charges on all capacitors, and (ii) a total charge measuring device outlet.

It is possible, but not necessary, that this particle energy measuring device comprises an analysis circuit that is configured to (i) effect a switching from one multiplexer input to another multiplexer input, so that the capacitors are individually discharged in succession, and (ii) detect the charge flowing from each capacitor during the discharging process, thereby obtaining charge data from which the particle energy can be calculated. The preferred embodiments of particle energy measuring devices specified above also apply for this invention.

Figure 2:
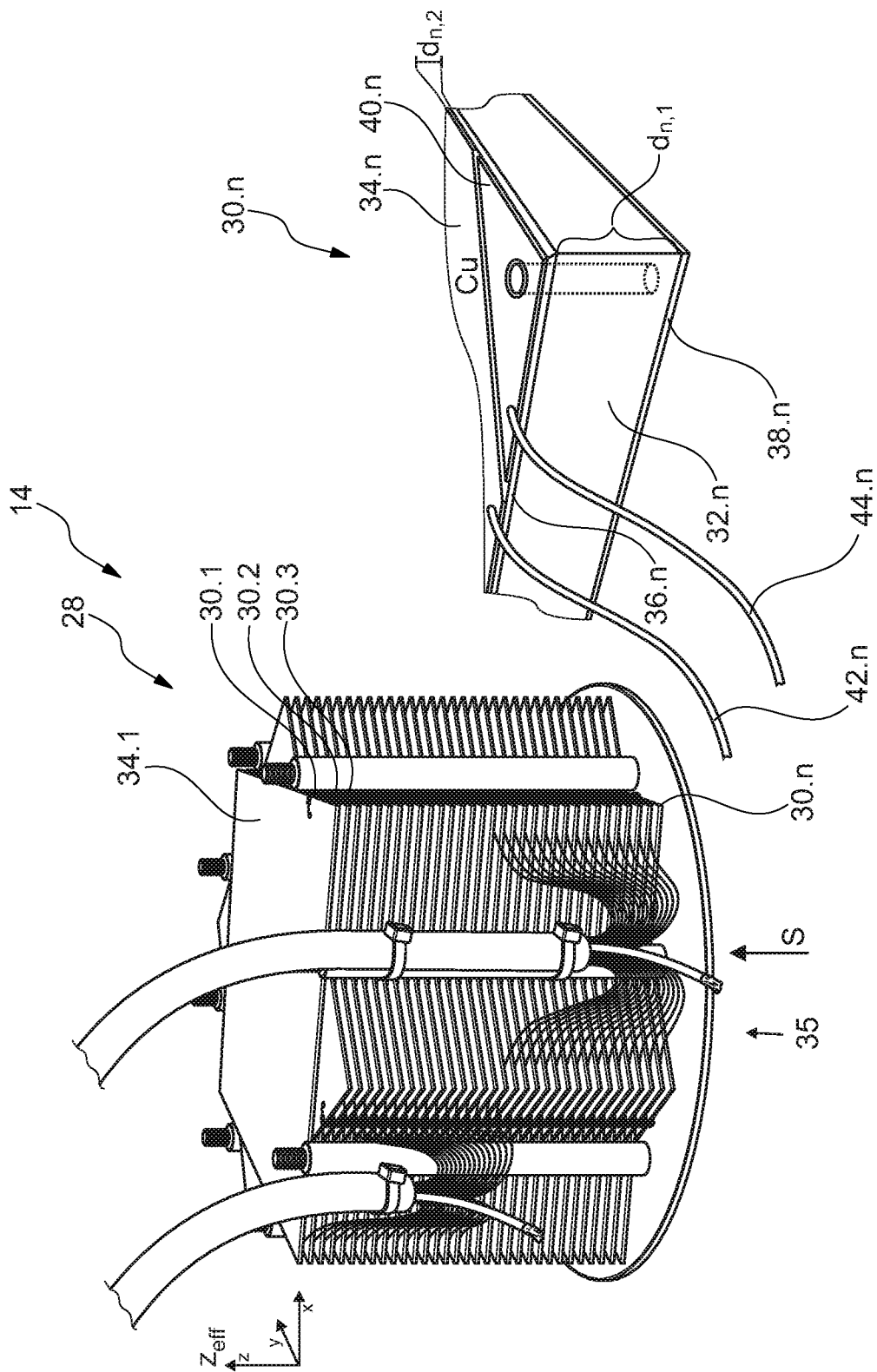
Figure 3:
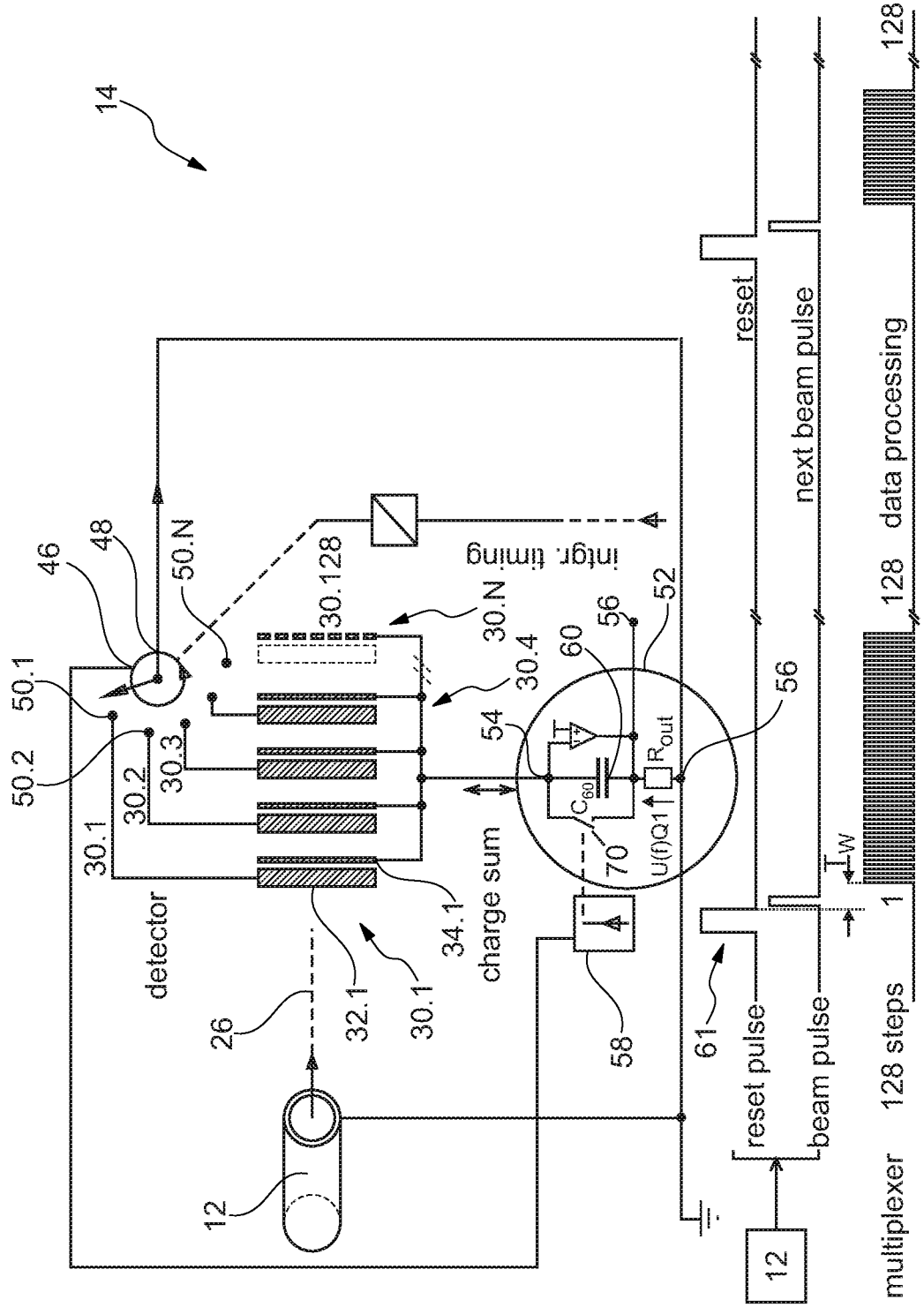
Figure 4:
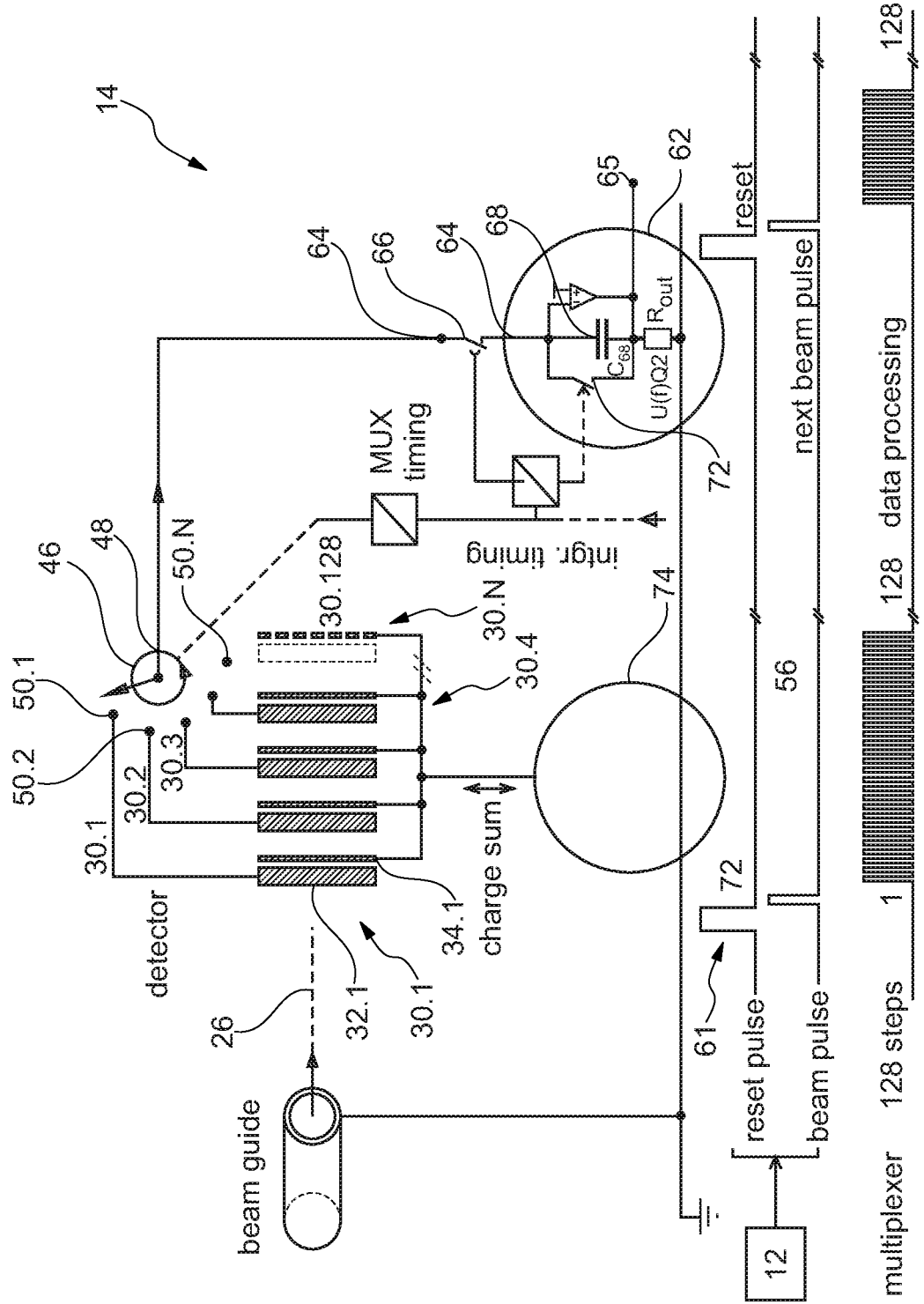
Figure 5:
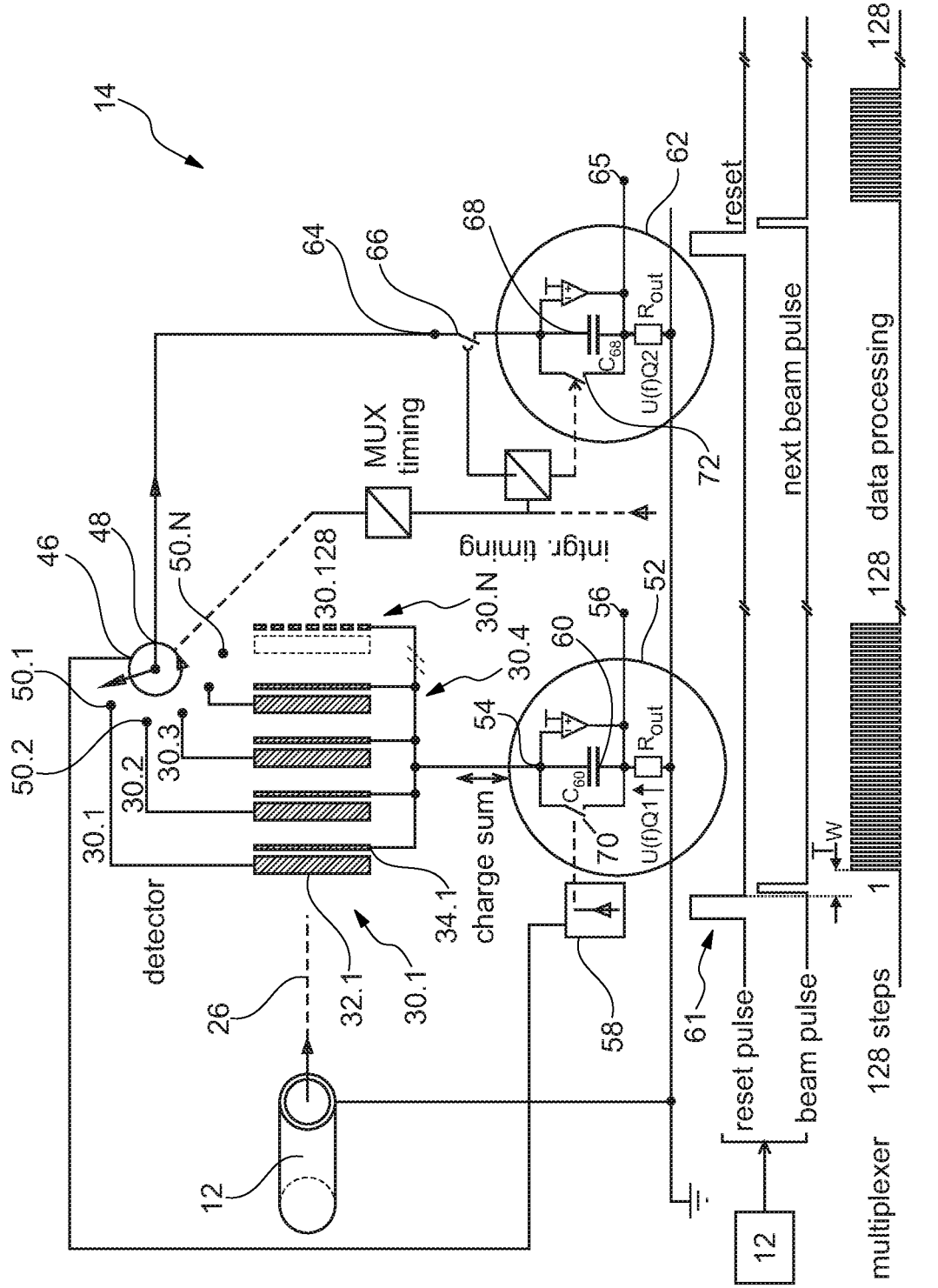
Figure 6A:
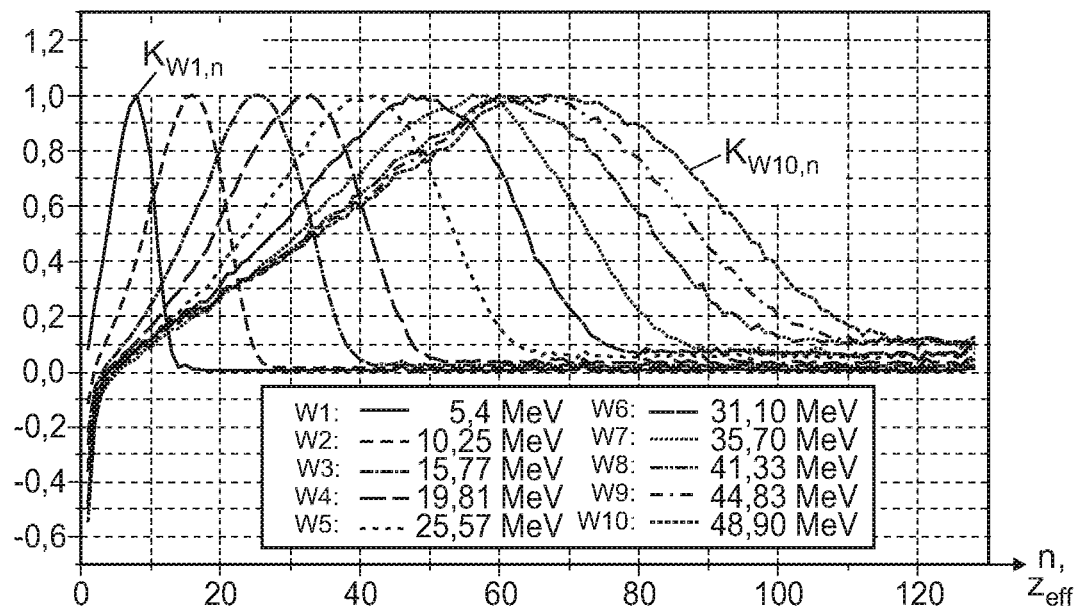
Figure 6B:
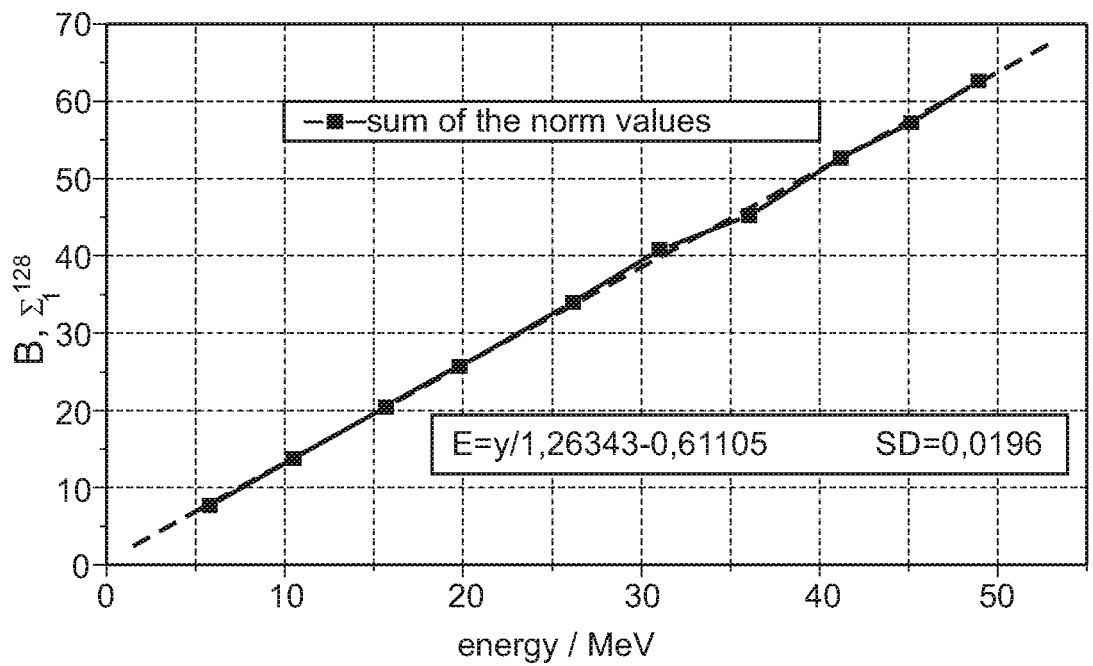
Figure 7:
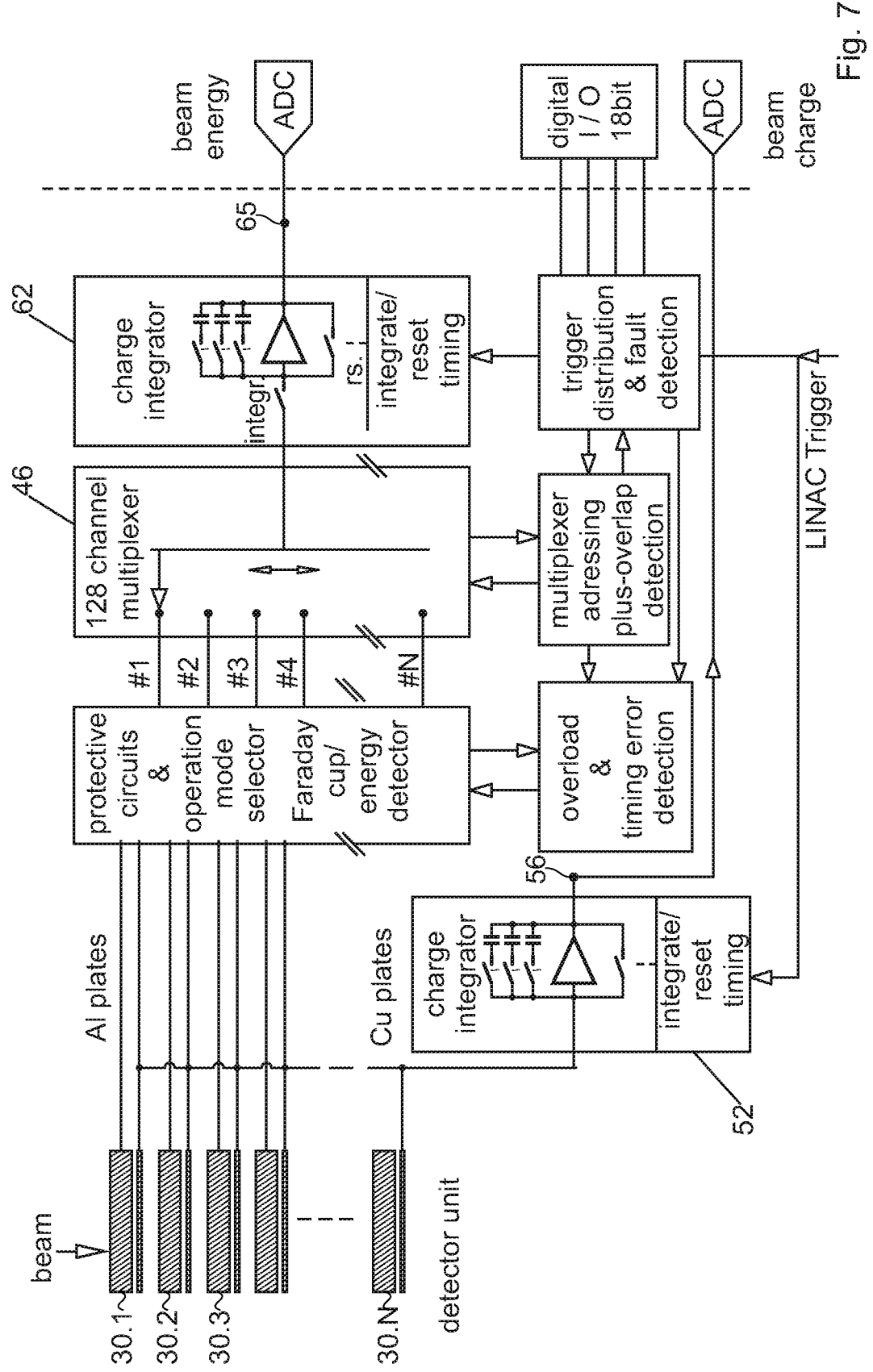
Figure 8:
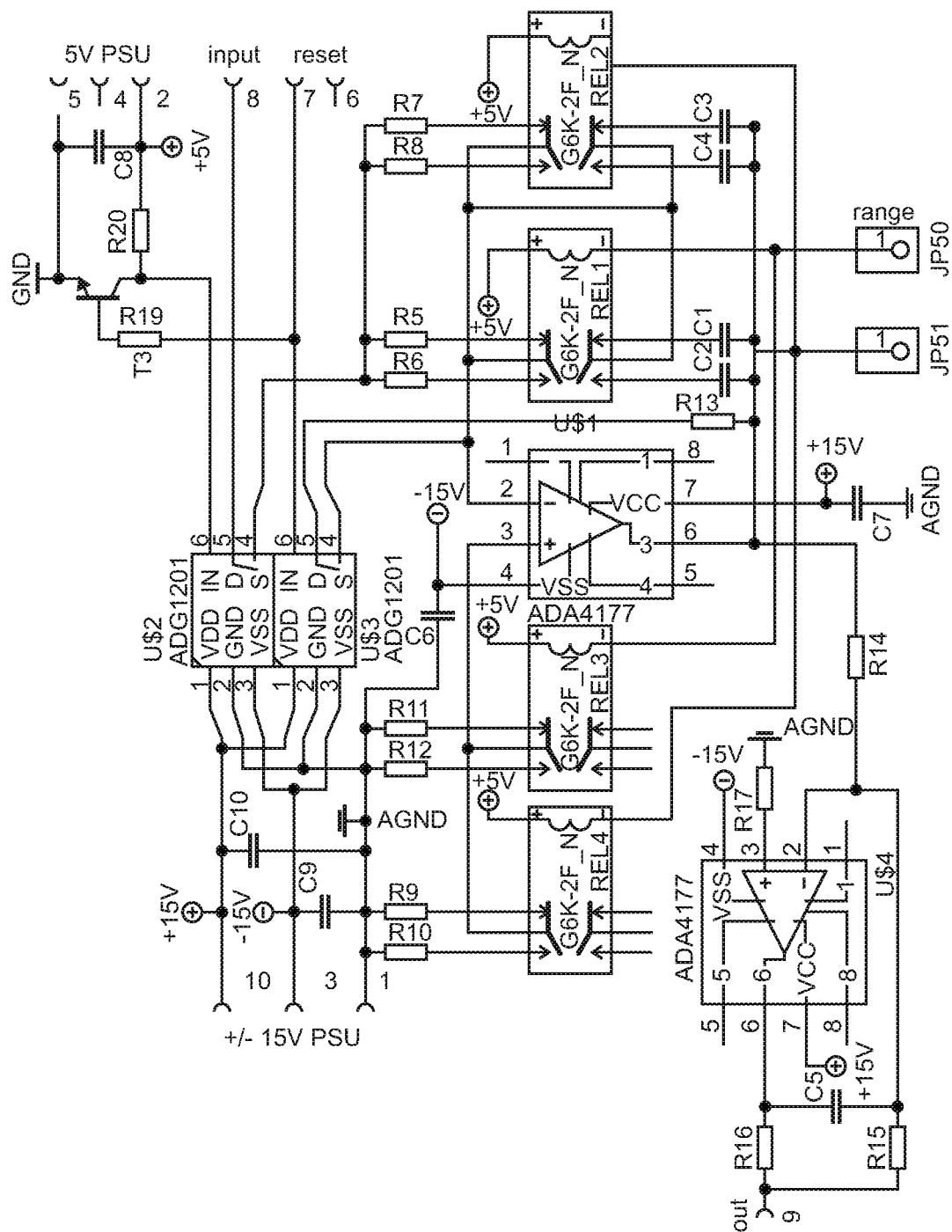

The invention will be explained in more detail by way of the attached figures. They show:

FIG. 1 an acceleration system according to the invention with a particle energy measuring device according to the invention, FIG. 2*a* a perspective view of a particle energy measuring device according to the invention, FIG. 2*b* a detailed view of a capacitor of the particle energy measuring device according to FIG. 2*a*, FIG. 3 a schematic circuit diagram of a particle energy measuring device according to the invention in accordance with a first embodiment, FIG. 4 a schematic circuit diagram of a particle energy measuring device according to the invention in accordance with a second embodiment, FIG. 5 a schematic circuit diagram of a particle energy measuring device according to the invention in accordance with a third embodiment, FIG. 6*a* a diagram in which the charge on the capacitors is plotted against the respective effective depth, FIG. 6*b* a diagram in which the width of the curve according to FIG. 6*a* is plotted against the particle energy, FIG. 7 a block diagram of an evaluation unit of the particle energy measuring device, and FIG. 8 a circuit diagram of the plate charge measuring device.

FIG. 1 shows an accelerator system 10 that comprises a particle accelerator 12, a particle energy measuring device 14 according to the invention and a spectrometer 16, which is optional. The spectrometer 16 is only used to calibrate the particle energy measuring device 14 and is therefore unnecessary after calibration when the accelerator system 10 is in use. The particle accelerator 12 can be quickly adjusted by means of the particle energy measuring device 14. Following adjustment, the particle energy measuring device 14 can be removed. The particle accelerator 12 is then ready for use.

The particle accelerator 12 is preferably an electron or proton accelerator. The particle accelerator 12 comprises a particle source 18, for example an electron source, a beam shaper 20 and two accelerator units 22.1, 22.2. The accelerator units 22.1, 22.2 are subjected to an HF alternating voltage by a klystron 24, wherein said voltage can have a frequency of F=3 GHz, for example. Frequencies between 1 and 5 GHz are possible. The phase shifters 26.1, 26.2 can be used to impose phase shifts $\varphi_1$, $\varphi_2$ on the RF power coupled to the buncher 20 and the first accelerator structure 22.1. An acceleration voltage is, for example, U=50 megavolts. The acceleration voltage is at least as high as the desired particle energy. It is a time-variable quantity and arises at the series resonance of the accelerator structure with the aid of the RF power of the klystron. Here, the resonance quality plays a part, as the following applies: U=Q $\sqrt{(P*Z)}$. A 3 GHz structure achieves a resonance quality Q of up to 20000. Particle accelerators 12 are well-known in the literature and shall therefore not be described in further detail.

The particle accelerator 12 generates a particle beam 26. It is beneficial if the particle accelerator 12 emits a mono-energectic particle beam. To this end, a monoenergetic particle beam is preferably generated from a non-monoenergetic particle beam by selection by means of energy slits after fanning by a dipole magnet. A monoenergetic particle beam is understood to mean a particle beam in which the individual particles barely deviate from the average particle energy. For example, in practice the deviation is at most ±5%, preferably at most ±0.5%.

FIG. 2a depicts a capacitor unit 28 of the particle energy measuring device 14 according to FIG. 1. The capacitor unit 28 comprises a plurality of capacitors 30.$n$ ($n$=1, 2, ..., N). The number N of capacitors is preferably at least 20, especially preferably at least 60. Each individual capacitor 30.$n$ has, as shown in FIG. 2b, a first capacitor plate 32.$n$, a second capacitor plate 34.$n$ and a solid dielectric 36.$n$ arranged between them, which is preferably a plastic plate. For example, the plastic plate is made of polyethylene terephthalate. The capacitor plates 32.$n$, 34.$n$ and the dielectric 36.$n$ are bonded together. It is beneficial if the capacitor 30 has, as in the present case, an insulator 38.$n$, which is also formed in the present case by a plastic plate. This plastic plate is bonded to the first capacitor plate 32.$n$. The capacitor unit 28 is created by stacking the capacitors 30.$n$ on top of each other and subsequent contacting.

FIG. 2b shows an especially simple way of contacting a capacitor 30.$n$. The first capacitor plate 32.$n$ is electrically connected to a contact region 40.$n$ (through-connection). The reason for this is that aluminum cannot be soldered easily. The problem can be solved by way of a contact region 40.$n$ made of a metal that can be effectively soldered, such as copper. The contact region 40.$n$ extends in the same plane as the second capacitor plate 34.$n$. As a result, the first capacitor plate 32.$n$ is electrically connected to the cable 44.$n$ and the second capacitor plate 34.$n$ with the second cable 42.$n$.

The first capacitor plate 32.$n$ is made of a first material that has a first density $\rho_{n,1}$. The second capacitor plate 34.$n$ is made of a material with a density $\rho_{n,2}$. In principle, it is possible that the densities of different capacitor plates 32.$a$, 32.$b$ ($a \neq b$) or 34.$a$, 34.$b$ ($a \neq b$) differ from each other. However, production is rendered especially easy when the respective materials are the same, so that the densities are also the same.

The density $\rho_{n,2}$ of the second capacitor is preferably greater than the density $\rho_{n,1}$ of the first capacitor plate. For example, the first capacitor plate 32.$n$ is made of aluminium or an aluminium alloy, the second capacitor plate 34.$n$ of copper or a copper alloy.

The first capacitor plate has a thickness of $d_{n,1}$, the second capacitor plate has a thickness of $d_{n,2}$. It is favorable if the thickness $d_{n,1}$ of the first capacitor plate 32.$n$ is greater than the thickness $d_{n,2}$ of the second capacitor plate 34.$n$. Preferably, the first capacitor plate 32 is the capacitor plate facing the beam, meaning that the capacitor plate 32.$n$ is in front of the second capacitor plate 34.$n$ in terms of a beam incidence direction S. An irradiation side 35 is at the front in the beam incidence direction S.

An effective thickness $D_{n,1} = \rho_{n,1,1} \cdot d_{n,1}$ of the first capacitor plate 32.$n$ is also greater than the effective thickness $d_{n,2}$ of the second capacitor plate 34.$n$. It is possible, but not necessary, that this applies for all capacitors 30.$n$.

FIG. 3 depicts a circuit diagram of the particle energy measuring device 14 according to the invention with the capacitors 30.$n$. The particle energy measuring device 14 also has a multiplexer 46, which features a multiplexer outlet 48 and a plurality of multiplexer inputs 50.$n$. Each multiplexer input 50.$n$ is designed to be connected to precisely one capacitor 30.$n$.

The particle beam 26 strikes the capacitors 30.$n$ and there generates charges $Q_n$.

The particle energy measuring device 14 has a total charge measuring device 52, which has a total charge measuring device input 54 and a total charge measuring device outlet 56. The total charge measuring device input 54 is connected to the second capacitor plate 34.$n$. If the multiplexer input 50.$n$ is connected to the respective capacitor 30.$n$, charges can flow via the total charge measuring device input 54 and the multiplexer outlet 48, so that the charge flows from the capacitor 30. The voltage Un acting on the nth capacitor 30.$n$ is thus reduced to zero or close to zero. The fact that the voltage Un is reduced to close to zero should be understood particularly to mean that any remaining voltage is so small that the measurement uncertainty increases by a relative 10%. A capacity C1 of a capacitor 60 of the total charge measuring device 52 is preferably C1=1nF to C1=10 µF.

FIG. 3 also shows that the particle energy measuring device 14 comprises an analysis circuit 58 that is connected to the multiplexer 56 for switching the multiplexer inputs 50.$n$. The analysis circuit 58 is also connected to the total charge measuring device 52 and automatically registers the change in a total charge $Q_\Sigma$ stored in the total charge measuring device 52. In particular, the total charge $Q_\Sigma$ on a capacitor 60 of the total charge measuring device 52 is detected. If a predetermined capacitor 30.$n$ is discharged, the total charge $Q_\Sigma$ changes by a difference $\Delta Q_\Sigma$. This difference $\Delta Q_\Sigma = Q_n$ corresponds to the charge $Q_n$ that was stored on the respective capacitor 30.$n$.

If the analysis circuit 58 receives a trigger signal 61 from the particle accelerator 12 (cf. FIG. 1), the total charge measuring device is reset by short-circuiting the capacitor 60 and detects the next total charge $Q_\Sigma$ on the total charge measuring device 52 during the waiting time Tw. During the waiting time and until the total charge $Q_s$ is read, the multiplexer input 50 is not connected to any capacitor 30.$n$.

Once the waiting time Tw has lapsed, the analysis circuit 8 automatically connects the multiplexer input 50.1 in succession to the first capacitor plate 32.$n$ of the capacitors 30$n$. Following connection to a capacitor 0.$n$, the change $Q_n = \Delta Q_s$, i.e. the change in the total charge $Q_s$ due to the discharging of the respective capacitor 30.$n$, is measured. The corresponding charge information represents charge data that encode the respective charges $Q_n$ on the nth capacitor. As explained below, this is used to determine the particle energy.

FIG. 5 depicts a second embodiment of a particle energy measuring device 14 according to the invention that features a plate charging measuring device 62. The plate charge measuring device 62 has a plate charge measuring device input 64, which can be connected to the multiplexer outlet 48 via the first switch 66, and a plate charge measuring device outlet 65. A measurement range capacitor 68 of the plate charge measuring device 62 can be bypassed via a second switch 72 of the plate charge measuring device 62, so that the capacitor 68 discharges. The capacity $C_{68}$ depends on the anticipated plate charge $Q_n$. As a combination of multiple measurement range capacitors, it can be switched freely and is selected in such a way that the voltage $U=Q/C$ at the outlet of the plate charge measuring device 62 does not exceed a limit of 10 Volt.

The plate charge measuring device 62 is connected to the analysis circuit 58, wherein this connection is not depicted for the sake of clarity. If the total charge $Q_\Sigma$ exceeds a predetermined limit $Q_{\Sigma,max}$, the analysis circuit 58 controls the multiplexer 46 in such a way that it successively connects the capacitors 30.n to the plate charge measuring device 62.

When switch 66 is closed and switch 72 is open, a charge balancing occurs on the respective plate capacitor 30.n. The charge $Q_n$ required for the balancing is detected by the plate charge measuring device 62 and appears at the outlet 65 as the voltage equivalent to this charge. This voltage is digitalized by the analysis circuit 58.

Switch 66 is then re-opened, switch 72 closed, and the multiplexer 46 connected to the next plate capacitor 30.n+1. The cycle repeats N times until the charge on the last plate capacitor 30.N is balanced and thus measured. Each time, closing the switch 72 discharges the measurement range capacitor 68. Opening the switch 66 immediately beforehand prevents the return flow of the charge towards the multiplexer 46.

The analysis circuit is preferably designed to automatically close the switches 66, 70, 72 when the trigger signal 61 does not occur for at least a predetermined shut-off period.

FIG. 4 shows a further embodiment of a particle energy measuring device 14 according to the invention that does not have a total charge measuring device 52, but instead features a single safety circuit 74 that short circuits all capacitors 30.n when a limit for the total charge is exceeded.

FIG. 6a depicts a diagram in which the charge $Q_n$ of the nth capacitor on the y axis is plotted against the respective capacitor 30.n on the x axis. In the present case, all capacitors 30.n are identical in structure, so that the running index n of the capacitors also represents an effective depth.

FIG. 6a depicts normalized charge functions $K_w$, which refer to the respective energy W. The charge curves $K_w$ are normalized, meaning that their maximum value is 1.

FIG. 6b shows the dependency of a width B of the respective charge curve $K_w$ on the (average) particle energy E. The width B is calculated as the numerical integral over the normalized charge curve $K_w$. Using a width calibration factor k in the form of the proportionality factor in the equation $W=k\cdot B+b$ and an axis section b, the particle energy can be calculated from any width B. In the present case, it holds for the width calibration that $k=1.2634$ and for the axis section that $b=0.61105$.

FIG. 7 depicts a block diagram of the analysis circuit 58.

FIG. 8 shows the circuit diagram of the second charge measuring device 62. The circuit of the total charge measuring device 52 is in essence identical: only the pins 4-5 of component U$2 have been bypassed because the total charge measuring device does not need the input switch.

REFERENCE LIST 10 accelerator system
12 particle accelerator
14 particle energy measuring device
16 spectrometer
18 particle source
20 beam shaper
22 accelerator unit
24 klystron
26 particle beam
28 capacitor unit
30 capacitor
32 first capacitor plate
34 second capacitor plate
35 irradiation side
36 dielectric
38 insulator
40 contact region
41 connector
42 first cable
44 second cable
46 multiplexer
48 multiplexer outlet
50 multiplexer input
52 total charge measuring device
54 total charge measuring device input
56 total charge measuring device outlet
58 analysis circuit
60 capacitor
61 trigger signal
62 plate charge measuring device
64 plate charge measuring device input
65 plate charge measuring device outlet
66 switch
68 second capacitor
70 second switch
72 third switch
74 safety circuit
b axis section
B width
C capacity
$\Delta Q_\Sigma$ difference
$d_{n,1}$ thickness of the first capacitor plate of nth capacitor
$D_{n,1}$ effective thickness of the first capacitor plate of the nth capacitor
$K_w$ charge function
n running index
N number of capacitor
$Q_n$ charge on the nth capacitor
$Q_\Sigma$ total charge
$\rho_{n,1}$ density of the first capacitor plate
S beam incidence direction
$T_W$ waiting time
$U_n$ voltage at the nth capacitor
E particle energy

The invention claimed is:

1. A particle energy measuring device for determining the energy of a particle beam with comprising
 (a) at least twenty capacitors that
  (i) each comprise a first capacitor plate and
  (ii) each comprise a second capacitor plate and
  (iii) are arranged one behind the other with respect to a beam incidence direction,
 (b) a multiplexer that
  (i) has a multiplexer outlet and
  (ii) has a plurality of multiplexer inputs, each multiplexer input being configured to connect to precisely one of the at least twenty capacitors and (iii) is configured to connect one of the first and second capacitor plates of the respective capacitor of the at least twenty capacitors to the multiplexer outlet,
(c) a total charge measuring device that comprises
  (i) a total charge measuring device input, which is connected to the second capacitor plates for detecting a total charge ($Q_\Sigma$) of the charges on all of the at least twenty capacitors, and
  (ii) a total charge measuring device outlet, and
(d) an analysis circuit which is connected to the total charge measuring device and the multiplexer and is configured to automatically
  (i) effect a switch from one of the multiplexer inputs to another of the multiplexer inputs, so that the at least twenty capacitors can be successively discharged, and
  (ii) detect a charge ($Q_n$) flowing from each of the at least twenty capacitors during the discharging process, thereby obtaining charge data from which the particle energy (E) is calculatable.

2. The particle energy measuring device according to claim 1, wherein the analysis circuit is configured to automatically conduct the following step:
  (i) for each position of the multiplexer, detecting the charge ($Q_n$) flowing from the respective capacitor by forming the difference ($\Delta Q_\Sigma$) between a charge on the total charge measuring device at a beginning and end of the discharging process of the respective capacitor, thereby obtaining charge data,
  (ii) wherein the charge data encode the charge ($Q_n$) of each of the at least twenty capacitors and the respective capacitors.

3. The particle energy measuring device according to claim 2, wherein
  the analysis circuit is configured to control the multiplexer, so that the multiplexer successively discharges the capacitors upon receiving a trigger signal.

4. The particle energy measuring device according to claim 1, further comprising
(a) a plate charge measuring device that
  (i) comprises a plate charge measuring device input, which is connected to the multiplexer outlet, and
  (ii) comprises a plate charge measuring device outlet, and
  (iii) is configured to measure a charge that flows via the multiplexer outlet and the plate charge measuring device input,
(b) wherein the analysis circuit
  (i) is connected to the total charge measuring device and the multiplexer, and
  (ii) is configured to automatically detect the charge flowing from each capacitor by detecting the charge measured by the plate charge measuring device, thereby obtaining charge data.

5. The particle energy measuring device according to claim 4, wherein the analysis circuit is configured to automatically determine the charges ($Q_n$) of the at least twenty capacitors in succession when the charge measured by the plate charge measuring device has exceeded a predetermined limit.

6. The particle energy measuring device according to claim 3, wherein the analysis circuit is configured to automatically discharge the at least twenty capacitors when the trigger signal does not occur for a predetermined shut-off period.

7. The particle energy measuring device according to claim 1, wherein the analysis circuit is configured to automatically calculate the particle energy (E) from the charge data by the following steps:
  (i) determining a width parameter (B) of the charge function (KW) and
  (ii) determining the particle energy (E) from the width parameter (B).

8. The particle energy measuring device according to claim 1, wherein at least a majority of the at least twenty capacitors have one or more of the following properties
  (a) a specific capacity (C) is 30 to 100 Picofarad per square centimeter,
  (b) a capacity (Cn) is at least 1 Nanofarad,
  (c) an insulation resistance between the first capacitor plate and the second capacitor plate is at least 1 G$\Omega$, and
  (d) the capacity (Cn) of the capacitor is greater than an intermediate capacitor capacity between capacitor plates of adjacent capacitors.

9. The particle energy measuring device according to claim 1, wherein at least a majority of the first capacitor plates is predominantly made of copper and/or aluminium.

10. The particle energy measuring device according to claim 1, wherein
  (a) the particle energy measuring device has an irradiation side and
  (b) an area-related ($\rho_n$) of the first capacitor plate on the irradiated side is at least five times greater than an area-related density ($\rho_n$) of the first capacitor plate of the capacitor facing away from the beam.

11. The particle energy measuring device according to claim 1,
  wherein at least for a majority of the at least twenty capacitors an effective thickness ($D_n$) of a capacitor plate facing away from the beam is smaller than the effective thickness ($D_n$) of a beam-side capacitor plate, wherein the capacitor plate facing away from the beam is one of the first or second capacitor plates, and the beam-side capacitor plate is the other of the first or second capacitor plates.

12. The particle energy measuring device according to claim 1,
  wherein for at least two capacitors of the at least twenty capacitors, the at least two capacitors including a capacitor facing away from the beam and a beam-side capacitor, an effective thickness ($D_n$) of at least one of the first and second capacitor plates of the capacitor facing away from the beam is greater than the effective thickness ($D_n$) of at least one of the first and second capacitor plates of the beam-side capacitor.

13. The particle energy measuring device according to claim 1, further comprising a calibration certification in which
  (a) the measurement uncertainty for at least one particle energy (E) and/or
  (b) a width calibration factor (K), from which the particle energy (E) can be calculated from width parameter (B), is indicated.

14. The particle energy measuring device according to claim 1, wherein the analysis circuit is configured to effect a discharge of the at least twenty capacitors if the supply charge ($Q_\Sigma$) exceeds a predetermined limit ($Q_\Sigma$,max).

15. An accelerator system with
  a particle accelerator for generating a particle beam, and
  a particle energy measuring device according to claim 1, that is arranged to measure a particle energy (E) of particles of the particle beam and/or a beam charge of the particle beam.

16. The particle energy measuring device of claim 8, wherein the capacity (Cn) is at least 7 Nanofarad.

17. The particle energy measuring device of claim 8, wherein the capacity (Cn) is at most 100 Nanofarad.

18. The particle energy measuring device of claim 8, wherein the capacity (Cn) of the capacitor is greater than the intermediate capacitor capacity by a factor of at least 5.

19. The accelerator system of claim 15, wherein the particle beam is a monoenergetic particle beam.

20. A method for determining a beam energy of a particle beam comprising the steps:
(a) allowing the particle beam to fall on a particle energy measuring device that comprises
(i) at least twenty capacitors that
each comprise a first capacitor plate and
each comprise a second capacitor plate and
are arranged one behind the other with respect to a beam incidence direction,
(ii) a multiplexer that has
a multiplexer outlet and
a plurality of multiplexer inputs, wherein each multiplexer input is connectable to precisely one of the at least twenty capacitors and
wherein said multiplexer is configured to connect one of the first and second capacitor plates of the respective capacitor of the at least twenty capacitors to the multiplexer outlet,
(iii) a total charge measuring device that comprises
a total charge measuring device input, which is connected to the second capacitor plates, and
a total charge measuring device outlet,
(b) successively measuring capacitor charges ($Q_n$) by the total charge measuring device by measuring a change in a total charge ($Q_\Sigma$) during the discharge process of the respective capacitor, thereby obtaining charge data, and
(c) calculating particle energy (E) and/or a beam charge from the charge data.

21. The method according to claim 20, wherein the successive measurement of the charges ($Q_n$) of the at least twenty capacitors is achieved
(a) by switching the total charge measuring device to detect a total charge ($Q_\Sigma$) of all charges on the at least twenty capacitors,
(b) successively discharging all of the at least twenty capacitors and
(c) measuring the decrease in the total charge ($Q_\Sigma$) for the discharge of one capacitor at a time.

22. The method according to claim 20, wherein
the particle beam is made up of particles with an average particle energy and
the first and second capacitor plates together exhibit such a thickness (d) that a total collecting efficiency for particles with the average particle energy is at least 96%.

23. The method according to claim 20, wherein the particle beam is composed of charged particles.

24. The method according to claim 20, wherein the average particle energy
(a) is between 2 MeV and 500 MeV if the particles are electrons, and
(b) is between 20 MeV and 1000 MeV if the particles are protons or ions.

25. The method according to claim 23, wherein the particle beam is composed of an electron beam, a proton beam, or an ion beam.

26. A method for determining a beam energy of a particle beam comprising the steps:
(a) allowing the particle beam to fall on a particle energy measuring device that comprises
(i) at least twenty capacitors that
each comprise a first capacitor plate and
each comprise a second capacitor plate and
are arranged one behind the other with respect to a beam incidence direction,
(ii) a multiplexer that has
a multiplexer outlet and
a plurality of multiplexer inputs, wherein each multiplexer input is connectable to precisely one of the at least twenty capacitors and
wherein said multiplexer is configured to connect a first capacitor plate of the respective capacitor to the multiplexer outlet,
(iii) a plate charge measuring device that comprises
a plate charge measuring device input, which is connected to the second capacitor plates, and
a plate charge measuring device outlet,
(b) successively measuring the capacitor charges ($Q_n$) by the plate charge measuring device by successively connecting the at least twenty capacitors to the plate charge measuring device using the multiplexer, thereby obtaining charge data, and
(c) calculating particle energy (S) and/or a beam charge ($Q_{26}$) from the charge data.

27. A particle energy measuring device for determining the energy of a particle beam with
(a) at least twenty capacitors that
(i) each comprise a first capacitor plate and
(ii) each comprise a second capacitor plate and
(iii) are arranged one behind the other with respect to a beam incidence direction,
(b) a multiplexer that
(i) has a multiplexer outlet and
(ii) has a plurality of multiplexer inputs, wherein each multiplexer input is connected to precisely one of the at least twenty capacitors and
(iii) said multiplexer is configured to connect a first capacitor plate of the respective capacitor of the at least twenty capacitors to the multiplexer outlet,
(c) a plate charge measuring device that comprises
(i) a plate charge measuring device input, which is connected to the multiplexer outlet, and
(ii) a plate charge measuring device outlet, and
(iii) wherein the plate charge measuring device is configured to measure a charge ($Q_n$) that flows via the multiplexer outlet and the plate charge measuring device input
(d) an analysis circuit which is connected to the plate charge measuring device and the multiplexer and is configured to automatically
(i) effect a switch from one of the multiplexer inputs to another of the multiplexer inputs, so that the at least twenty capacitors can be successively discharged, and
(ii) detect a charge ($Q_n$) flowing from each of the at least twenty capacitors during the discharging process, thereby obtaining charge data from which the particle energy (E) is calculatable.

28. A particle energy measuring device for determining the energy of a particle beam with
- (a) at least twenty capacitors that
  - (i) each comprise a first capacitor plate and
  - (ii) each comprise a second capacitor plate and
  - (iii) are arranged one behind the other with respect to a beam incidence direction,
- (b) a multiplexer that has
  - (i) a multiplexer outlet and
  - (ii) a plurality of multiplexer inputs, wherein each multiplexer input is connected to precisely one of the at least twenty capacitors and
  - (iii) said multiplexer is configured to connect a first capacitor plate of the respective capacitor of the at least twenty capacitors to the multiplexer outlet,
- (c) a plate charge measuring device that comprises
  - (i) a plate charge measuring device input, which is connected to the multiplexer outlet, and
  - (ii) a plate charge measuring device outlet, and
  - (iii) wherein the plate charge measuring device is configured to measure a charge ($Q_n$) that flows via the multiplexer outlet and the plate charge measuring device input, and
- (d) a total charge measuring device that comprises
  - (i) a total charge measuring device input, which is connected to the second capacitor plates for detecting a total charge ($Q_\Sigma$) of the charges on all of the least twenty capacitors, and
  - (ii) a total charge measuring device outlet.

* * * * *